(12) United States Patent
Kim et al.

(10) Patent No.: US 7,771,513 B2
(45) Date of Patent: Aug. 10, 2010

(54) METHODS OF STORING AND SEPARATING GASES USING MICROPOROUS METAL FORMATES

(75) Inventors: Kimoon Kim, Pohang (KR); Hyunuk Kim, Pohang (KR); Kyeng Min Park, Pohang (KR); Denis G. Samsonenko, Pohang (KR); Yinyong Sun, Pohang (FR)

(73) Assignee: Postech Academy-Industry Foundation, Pohang, Kyungsangbuk-Do (KR)

( * ) Notice: Subject to any disclaimer, the term of this patent is extended or adjusted under 35 U.S.C. 154(b) by 365 days.

(21) Appl. No.: 12/026,004

(22) Filed: Feb. 5, 2008

(65) Prior Publication Data

US 2008/0184885 A1  Aug. 7, 2008

(30) Foreign Application Priority Data

Feb. 5, 2007  (KR) ...................... 10-2007-0011761

(51) Int. Cl.
*B01D 53/72* (2006.01)
(52) U.S. Cl. .......................................... 95/145; 95/138
(58) Field of Classification Search ................... 95/138, 95/145
See application file for complete search history.

(56) References Cited

U.S. PATENT DOCUMENTS

| | | | | |
|---|---|---|---|---|
| 4,917,711 A | * | 4/1990 | Xie et al. ...................... | 95/106 |
| 5,626,650 A | * | 5/1997 | Rodriguez et al. ............ | 95/116 |
| 5,648,508 A | | 7/1997 | Yaghi | |
| 5,779,767 A | * | 7/1998 | Golden et al. .................. | 95/96 |
| 5,846,295 A | * | 12/1998 | Kalbassi et al. ............... | 95/105 |
| 2005/0217483 A1 | * | 10/2005 | Shimada et al. ............... | 95/140 |

FOREIGN PATENT DOCUMENTS

KR   1020050052929 A   6/2005

* cited by examiner

*Primary Examiner*—Robert J Hill, Jr.
*Assistant Examiner*—Christopher P Jones
(74) *Attorney, Agent, or Firm*—Perman & Green LLP

(57) ABSTRACT

Provided are methods of storing and separating acetylene or oxygen using microporous metal formates having a three-dimensional structure of metal and formate ion (HCOO⁻). Microporous metal formates used in the method selectively and stably adsorb a large amount of a specific gas within its structure. Therefore, those methods can be used in industrial appliances related to, for example, synthesis and transportation of high-purity gas.

4 Claims, 9 Drawing Sheets

METHODS OF STORING AND SEPARATING GASES USING MICROPOROUS METAL FORMATES

CROSS-REFERENCE TO RELATED PATENT APPLICATIONS

This application claims the benefit of Korean Patent Application No. 10-2007-0011761, filed on Feb. 5, 2007, in the Korean Intellectual Property Office, the disclosure of which is incorporated herein in its entirety by reference.

BACKGROUND

1. Field

The disclosed embodiments relate to methods of storage and separation of gases using microporous metal formates, and more particularly, to a method of selectively separating acetylene, oxygen or others from a mixture of gases using microporous metal formates with 1D zig-zag channels and a method of storing acetylene, oxygen or others using microporous metal formates.

2. Description of the Related Art

Microporous metal formates are cheap, easily prepared porous metal-organic materials that contain one-dimensional zigzag channels with a narrow pore opening. Depending on metal ions, the aperture of metal formate is diverse but sufficient for passage of small gas molecules. Microporous metal formates can selectively adsorb gas molecules or small organic molecules according to window size and chemical conditions of the cavities thereof, and can be used for catalyst activity, storage of gases, ion exchange, and separation of mixtures.

Metal formates are well-known porous materials, and extensive research is currently being conducted to obtain materials having better characteristics than conventional zeolite by changing chemical environments of cavities of porous materials through a simple synthesis process. Porous materials having a large surface area and thermal stability can be prepared using an organic molecule that stably binds to many metallic ions at the same time (see U.S. Pat. No. 5,648,508). Such an organic molecule can be a carboxylic salt ($RCOO^-$) that can stably bind to two or more metallic ions at the same time. Such porous materials synthesized from metallic ions and organic molecules can be used as materials that can adsorb and store a large amount of hydrogen and methane. Currently, more research is being conducted to increase gas storage capacity to a practical level and to develop porous materials that selectively adsorbs a specific gas.

SUMMARY

The disclosed embodiments provide a method of storage of acetylene using microporous metal formates.

The disclosed embodiments also provide a method of selectively separating acetylene from a mixture of gases containing the acetylene using microporous metal formates.

The disclosed embodiments also provide a method of separation and storage oxygen using microporous metal formates.

According to an aspect of the disclosed embodiments, there is provided a method of storing acetylene, comprising contacting acetylene or an acetylene-containing gaseous mixture with microporous metal formates represented by Formula 1 so as to adsorb acetylene to microporous metal formates:

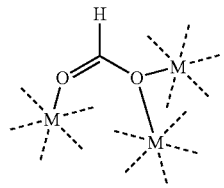

<Formula 1> where each formate ion is bound to three metallic ions Ms, each metallic ion M is bound to six formate ions, a composition ratio of the metallic ion M to the formate ion is 1:2, and the metal is Mg, Mn, Co, Zn, Ni or Fe.

According to another aspect of the disclosed embodiments, there is provided a method of separation of acetylene from an acetylene-containing gaseous mixture with microporous metal formates. The gaseous mixture may be contacted with microporous metal formates at a temperature of from 196K to 325K.

According to another aspect of the disclosed embodiments, there is provided a method of storage of oxygen from a gaseous mixture of nitrogen and oxygen with microporous metal formates so as to adsorb oxygen onto the microporous metal formates.

According to another aspect of the disclosed embodiments, there is provided a method of separating oxygen from a gaseous mixture of oxygen and nitrogen with microporous metal formates so as to selectively adsorb oxygen onto microporous metal formates.

The gaseous mixture containing oxygen may be contacted with the microporous metal formates at a temperature of from 77K to 325K.

According to the method of storing acetylene or oxygen according to the disclosed embodiments, gas molecules was adsorbed in cavities of microporous metal formates and thus, stably exist in a solid phase, and a great amount of gas can be stably stored. According to the method of separating acetylene or oxygen according to the disclosed embodiments, acetylene or oxygen can be selectively adsorbed out of the gaseous mixture and thus, high purity of acetylene, nitrogen or oxygen can be obtained.

BRIEF DESCRIPTION OF THE DRAWINGS

The above and other features and advantages of the disclosed embodiments will become more apparent by describing in detail exemplary embodiments thereof with reference to the attached drawings in which.

DETAILED DESCRIPTION

The disclosed embodiments will now be described more fully with reference to the accompanying drawings, in which exemplary embodiments of the disclosed embodiments are shown.

Microporous metal formates used in the disclosed embodiments are represented by Formula 1 and has a three-dimensional structure including cavities having predetermined sizes, wherein the cavities can selectively store acetylene or oxygen:

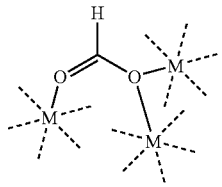

<Formula 1> where each formate ion is bound to three metallic ions Ms, each metallic ion M is bound to six formate ions, a composition ratio of the metallic ion M to the formate ion is 1:2, and the metal is Mg, Mn, Co, Zn, Ni, or Fe.

The microporous metal formates represented by Formula 1 and a method of preparing the same are disclosed in Korean Patent Application Pub. No. 2005-0052929, the disclosure of which is incorporated herein by reference in its entirety.

Figure 1:
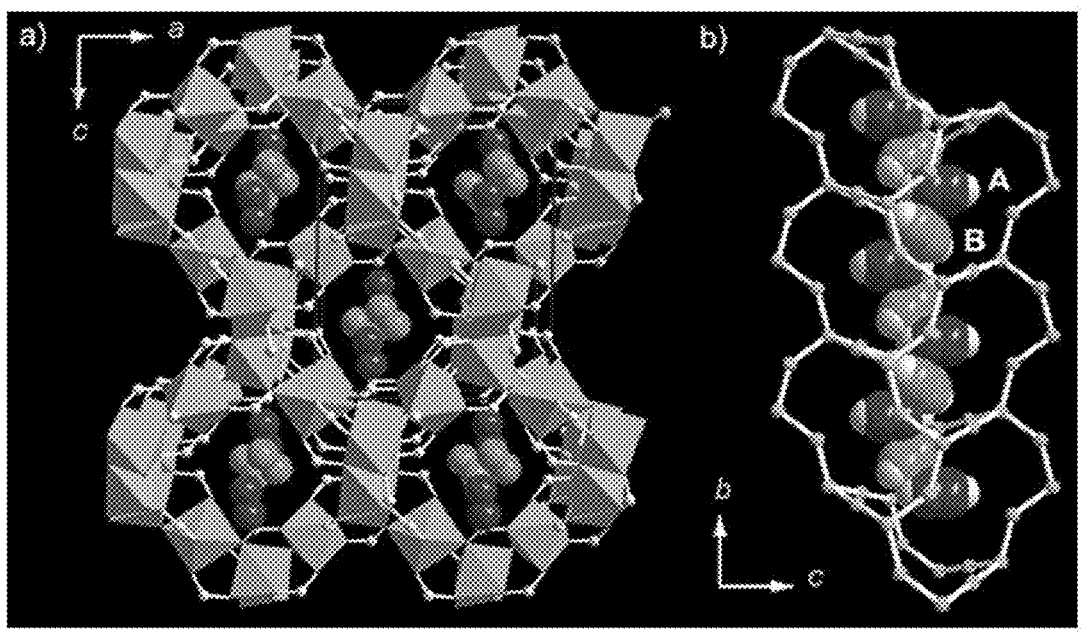
FIG. 1 is a photographic image showing a three-dimensional crystal structure of microporous metal formates which contain acetylene, obtained using an X-ray crystal structure analysis method.

FIG. 1 is a photographic image showing a three-dimensional crystal structure of a microporous metal formate containing acetylene, obtained using an X-ray crystal structure analysis method. Referring to FIG. 1, a) shows a plan view of the three-dimensional crystal structure, and b) shows a side view of the three-dimensional crystal structure. In the three-dimensional crystal structure, quadangular pyramids represent metals such as Mn, Mg or other metal ions, and small balls and sticks connected to each other represent formate ions. Referring to FIG. 1, cavities surrounded by metal and formate are regularly arranged, and acetylene molecules represented by large balls indicated by A and B are contained therein. b) Only metal ions and acetylene molecules are presented for clarity.

The surface area of microporous metal formates was determined using a BET method. The surface area of microporous Mn formate is approximately 284 $m^2/g$ and the surface area of microporous Mg formate is approximately 297 $m^2/g$. The dead volume of a microporous metal formate was measured using high-purity gaseous He. The pore volume ($V_p$) of a Mg-formate is 0.14 $cm^3g^{-1}$ and the pore volume ($V_p$) of Mn-formate is 0.13 $cm^3g^{-1}$. Therefore, microporous metal formates store large amount of acetylene gases.

The X-ray crystal structure of a microporous Mn-formate which contains acetylene has characteristics such as: monoclinic, $P2_1/n$, a=11.624(1)☐, b=10.165(1)☐, c=14.738(1)☐, β=91.402 (1)°, V=1740.9(3)☐³, Z=12, T=90 K, d(calculated value)=1.759 g/$cm^3$, $R_1$=0.0321, $wR_2$=0.0961, and GOF=1.069.

The X-ray crystal structure of a microporous Mg-formate which contains acetylene has characteristics such as: monoclinic, $P2_1/n$, a=11.315(1)☐, b=9.853(1)☐, c=14.400(1)☐, β=91.320 (1)°, V=1605.0(2)☐³, Z=12, T=90 K, d(calculated value)=1.527 g/$cm^3$, $R_1$=0.0374, $wR_2$=0.1084, and GOF=1.041.

Figure 2:
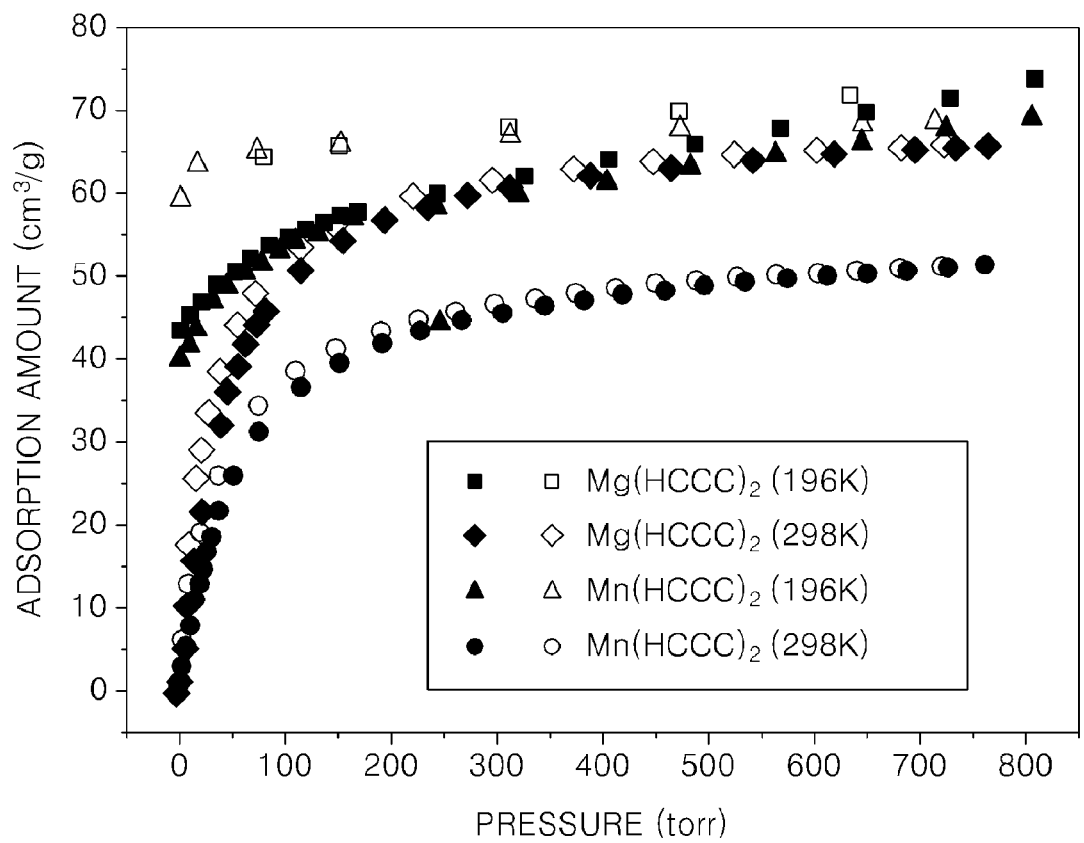
FIG. 2 is a graph showing adsorption acetylene isotherms of microporous metal formates at 196K and 298K.

FIG. 2 is a graph showing adsorption isotherms of a microporous metal formate onto which acetylene is adsorbed at temperatures of 196K and 298K. In FIG. 2, ■, ☐, ▲ and ● represent data with respect to acetylene adsorption, and ☐, ☐ ☐ and ○ represent data with respect to acetylene desorption. Amounts of acetylene adsorbed onto the microporous metal formate are shown in Table 1.

TABLE 1

| Microporous metal | Adsorption Amount of Acetylene $cm^3/g^{-1}$ ($cm^3/cm^{-3}$) | | |
|---|---|---|---|
| formate | 196 K | 275 K | 298 K |
| Mg-formate | 72.5 (101) | 69.4 (96.5) | 65.7 (91.3) |
| Mn-formate | 68.2 (112) | 57.7 (95.2) | 51.2 (84.5) |

Referring to FIG. 2, the Mn-formate adsorbed 51 $cm^3/g$ of acetylene at 1 bar (760 torr), and the microporous Mg-formate can adsorb 66 $cm^3/g$ of acetylene at room temperature. Such results show that the Mn-formate and the Mg-formate have better adsorption capacities than a known microporous organometallic material, [$Cu_2(pzdc)_2(pyz)$] which can adsorb 42 $cm^3/g$ of acetylene at 1 bar.

Referring to FIG. 2, Mn-formate and Mg-formate show hysteresis at 196K, and at low pressure, which means acetylene can be stored at low temperature and low pressure. In addition, microporous Mn formate and microporous Mg formate can adsorb a large amount of acetylene even at 295K or 298K and can stably contain gas molecules that are explosive at high pressure.

Acetylene can be stored safely using the storage method according to the disclosed embodiments, as described above here below, due to a containment state of acetylene contained in the microporous metal formate. In general, acetylene is stored in an organic solvent such as acetone or DMF. In a solution state, acetylene molecules collide with each other at high temperature at high pressure and thus explode. In the storage method according to the disclosed embodiments, a single acetylene molecule, as illustrated in FIG. 1, occupies a single metal-formate cavity and thus, acetylene molecules can be separated from each other. Therefore, the storage method according to the disclosed embodiments can minimize the risk of explosion occurring due to contact of acetylene molecules.

Therefore, in the method of storing acetylene according to the disclosed embodiments, an acetylene-containing gas can be trapped in microporous metal formates represented by Formula 1. The acetylene gas adsorbed onto the microporous metal formates can be recollected by, for example, increasing the temperature to 298K or more or decreasing the ambivalent pressure.

Meanwhile, in the method of storing acetylene according to the disclosed embodiments, referring to FIG. 2, acetylene is incompletely desorbed from the microporous metal formates even when the pressure is 0.1 bar (76 torr) or less (refer to results denoted by "☐"), and thus acetylene can be stored even at a pressure of 0.1 bar or less. In addition, even at a pressure of 1 bar or more, as illustrated in FIG. 1, acetylene can be safely stored without explosion because acetylene is contained in cavities of the microporous metal formate. The inventors of the disclosed embodiments found that acetylene can be stored even at a pressure of $10^{-5}$ bar in a predetermined temperature range, and also even at a pressure of 3 bar, acetylene can be stably stored without explosion.

Figure 3A:
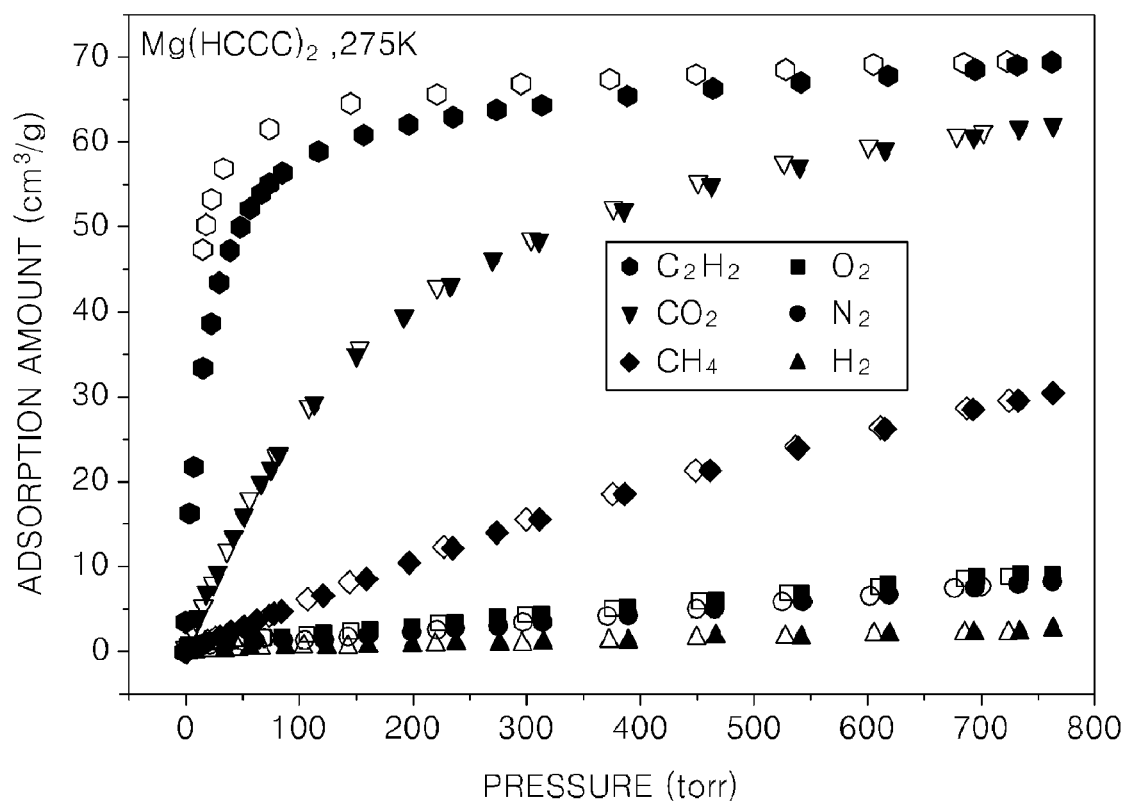
FIGS. 3A and 3B are graphs showing adsorption isotherms of various gases at 275K and 298K using microporous Mg formate.
Figure 3B:
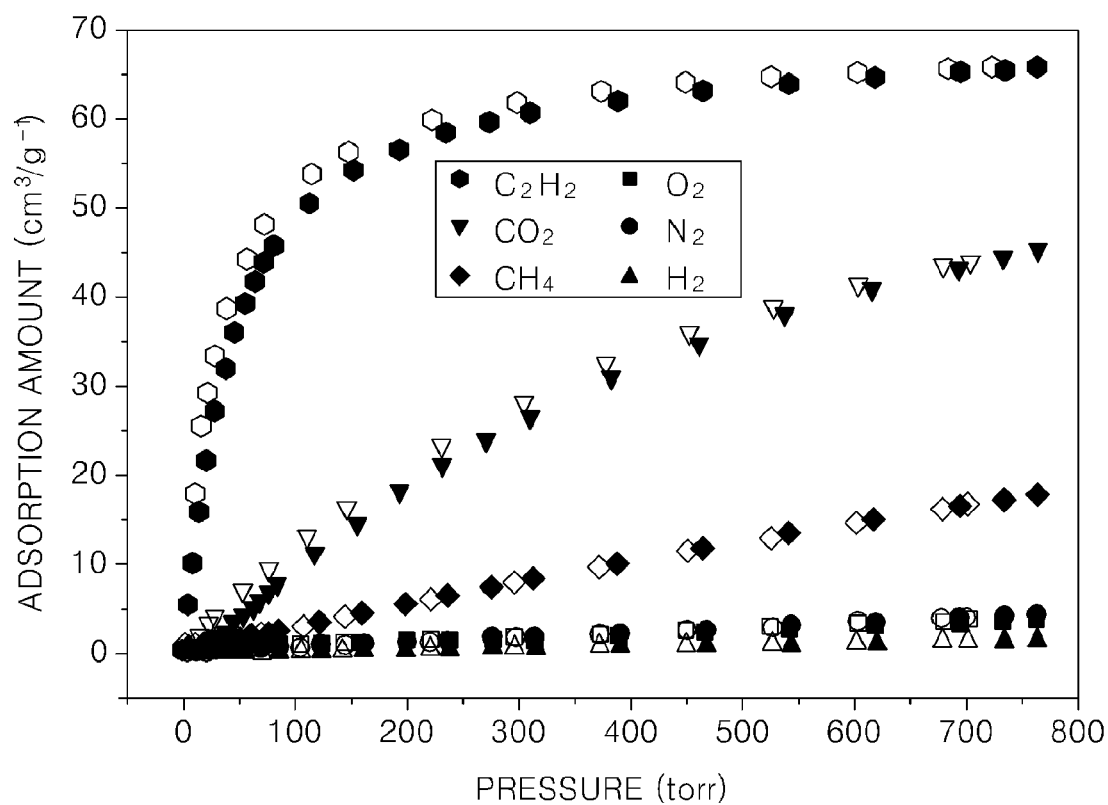
Figure 4A:
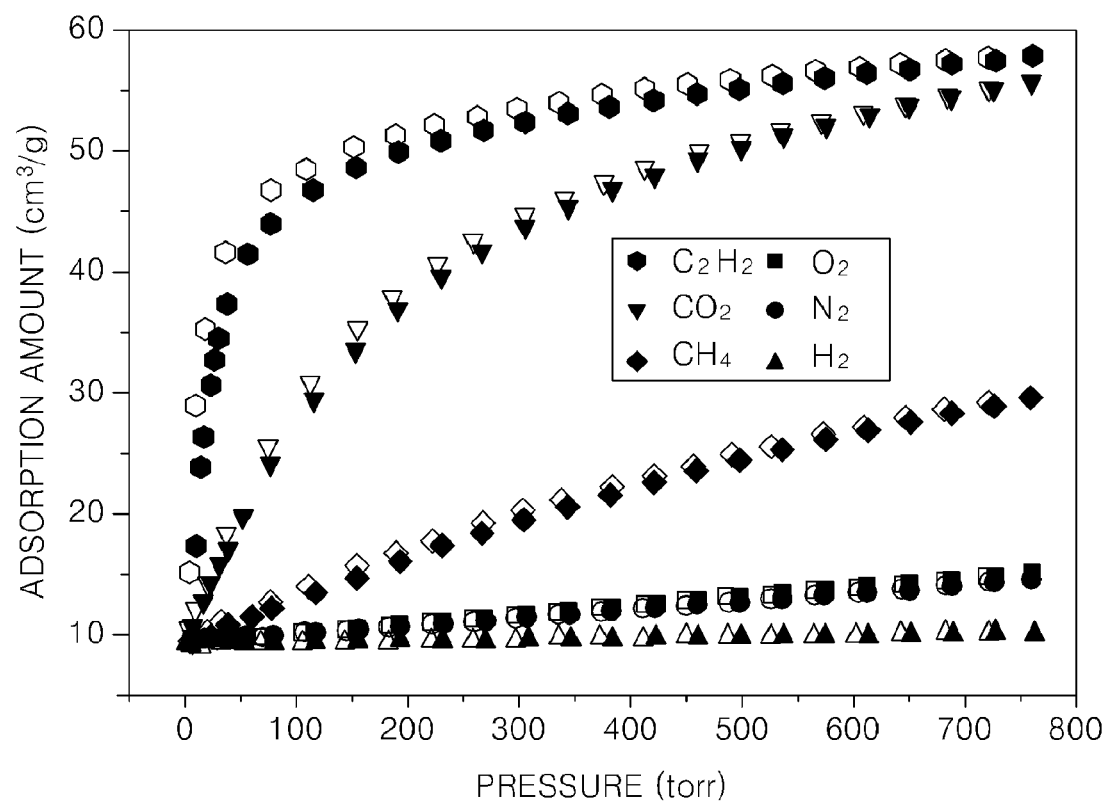
FIGS. 4A and 4B are graphs showing adsorption isotherms of various gases at 275K and 298K using microporous Mn formate.
Figure 4B:
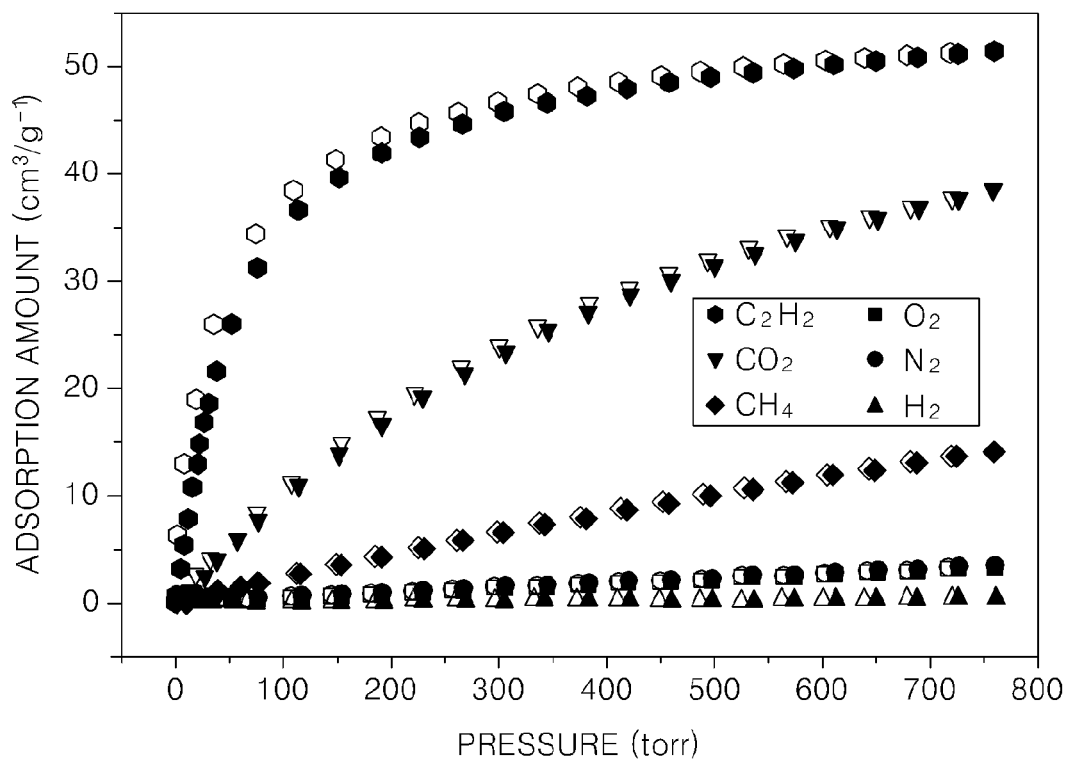

In the method of storing acetylene according to the disclosed embodiments, acetylene can be stored at a temperature of 298K or more, such as 325K. Comparing FIG. 3B with FIG. 3A and FIG. 4B with FIG. 4A, the amount of acetylene adsorbed onto the microporous metal formate is not decreased even at 298K with respect to that at 275K.

A method of separating acetylene according to the disclosed embodiments is derived from selective adsorption properties of microporous metal formates in which acetylene is adsorbed.

FIGS. 3A, 3B, 4A, and 4B show adsorption isotherms of various gases using microporous metal formates. In the drawings,

□, □, ○, □ and □ show data obtained with regard to desorption of acetylene, nitrogen, carbon dioxide, oxygen, methane and hydrogen. Referring to FIGS. 3A, 3B, 4A, and 4B, it can be seen that microporous metal formates adsorb acetylene the most.

Therefore, in the method of separating acetylene according to the disclosed embodiments, a microporous metal formate represented by Formula 1 contact with a gaseous mixture including acetylene, and acetylene is selectively adsorbed onto the porous crystalline material. The microporous metal formates have excellent adsorbing properties with respect to acetylene compared to those with respect to hydrogen, nitrogen, oxygen, methane, carbon dioxide, acetylene, monoxide, $SF_6$, $NO$, $N_2O$, $NO_2$, $H_2S$, $SO_2$, $Cl_2$, krypton, neon, zenon, and helium. Therefore, even when acetylene is mixed with those gases, acetylene can be selectively adsorbed and separated.

Meanwhile, the separating process of the acetylene may be performed in a temperature range from 196K to 325K. In general, acetylene is liquidized at a low temperature, but can be maintained in its gaseous state by reducing a pressure. In this state, acetylene can be separated from other gases using the separation method according to the disclosed embodiments. In the method of separating acetylene from other gases, acetylene can be more easily separated when a temperature increases. Referring to FIGS. 3A, 3B, 4A, and 4B, the amount of acetylene adsorbed onto the microporous metal formate at 298K is almost the same as the amount of acetylene adsorbed onto the microporous metal formate at 275K. On the other hand, the amount of other gases, such as $CO_2$ and methane, adsorbed onto the microporous metal formate at 298K is substantially less than the amount of other gases, such as $CO_2$ and methane, adsorbed onto the microporous metal formate at 275K. Meanwhile, although acetylene can be more easily separated as the temperature increases from 275K to 375K, the separation temperature may be 325K or less in consideration of the risk of explosion.

The separation and storage method of oxygen is derived from higher selective adsorption properties of microporous metal formates with respect to oxygen than those with respect to nitrogen at low temperature.

Figure 6:
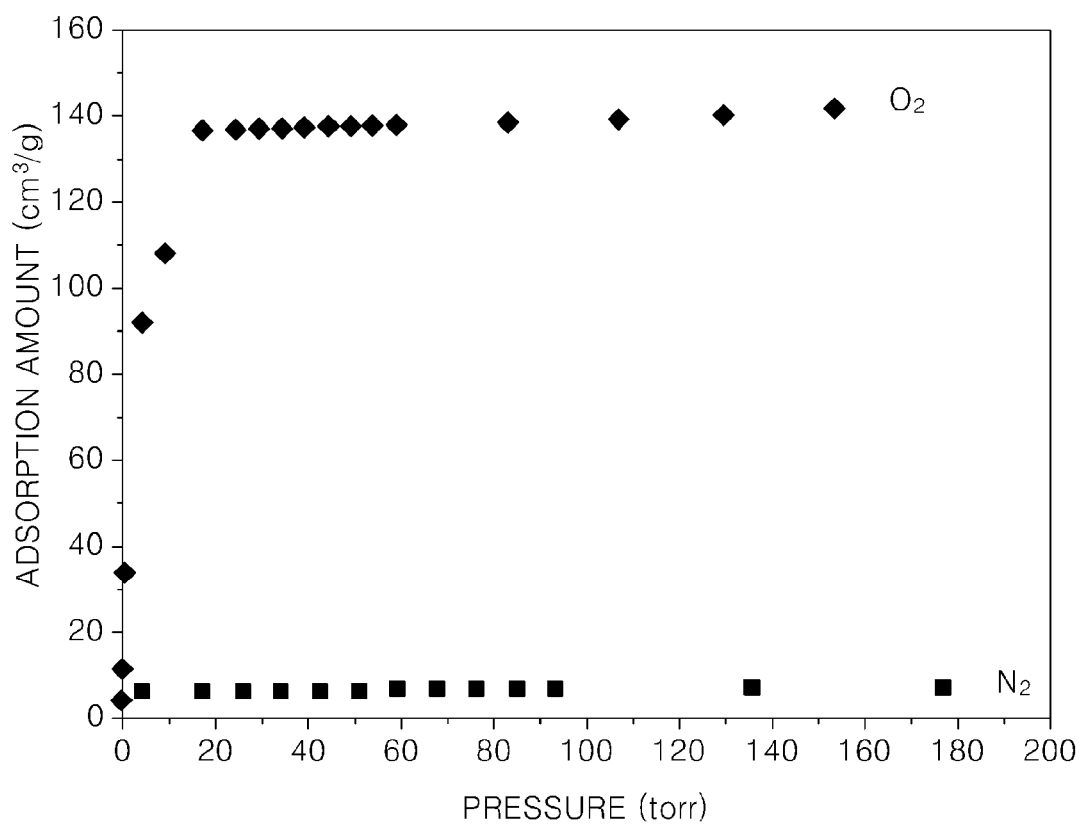
FIG. 6 is a graph showing adsorption isotherms of microporous Mn formate with respect to a gaseous mixture of oxygen and nitrogen at 77K.

FIG. 6 is a graph showing adsorption isotherms of a microporous metal-formate with respect to a gaseous mixture of oxygen and nitrogen at 77K. Referring to FIG. 6, it can be seen that the microporous metal formate adsorbs a much greater amount of oxygen compared to nitrogen.

Therefore, the separation and storage method of oxygen according to the disclosed embodiments includes contacting oxygen, or a gaseous mixture of oxygen and nitrogen with the microporous metal formate represented by Formula 1 so as to selectively adsorb oxygen.

In methods of separating and storing oxygen according to the disclosed embodiments, the microporous metal formate can be contacted to oxygen at a temperature range from 77K to 150K. In general, oxygen can be liquidified when the temperature is less than 77K. However, even at 77K, the liquidfication can be prevented by maintaining a pressure of, for example, 156 torr or less. Meanwhile, when the temperature is higher than 150 K, a Van der Waals force between nitrogen and oxygen and the microporous metal formate is decreased, the adsorption properties of the microporous metal formate may be decreased, and thus, the separating properties of the microporous metal formate is decreased.

As described above, the methods of storing and separating acetylene or oxygen according to the disclosed embodiments are suitable for preparation and storage of high-purity gas because the microporous metal formate of Formula 1 selectively adsorbs a large amount of gas at low temperature or room temperature and enables the storage and separation of the gas.

The disclosed embodiments will be described in further detail with reference to the following examples. These examples are for illustrative purposes only and are not intended to limit the scope of the disclosed embodiments.

EXAMPLES

Example 1

Storage of Acetylene Using Microporous Metal Formate

Microporous Mn-formate and Mg-formate were synthesized with reference to Example 1 of Korean Patent Application Pub. No. 2005-0052929. The microporous metal formates were vacuum-dried at 200 □ for 2 days to remove 1,4-dioxane existing as a guest molecule. An adsorption device of acetylene was Autosorp-1-MP of Quantachrome. A saturated vapor was initially fixed at 763 torr and the pressure of acetylene was increased from $10^{-5}$ atm to 1 atm.

When the pressure was not changed by 0.0008 atm or more for the equilibrium time of 3 minutes, the pressure was measured so as to calculate the volume of acetylene adsorbed onto microporous metal formates with respect to each adsorption or desorption data point.

A dry ice/acetone mixture was used to maintain the temperature at 196 K. A temperature of 275K was maintained using ice water, and a temperature of 298K was maintained using water bath.

The amount of acetylene contained in the microporous metal formate is illustrated in FIG. 2 in the form of an adsorption isotherm.

Referring to FIG. 2, the microporous metal formate adsorbs a maximum of 72.5 $cm^3$/g of acetylene. Therefore, it can be seen that the microporous metal formate has excellent storage properties of acetylene.

Example 2

Separation of Acetylene Using Microporous Metal Formates (1) Adsorption isotherms of various gases using microporous metal formates. A graph of adsorption isotherms in which various gases were adsorbed was obtained using the same manner as in Example 1 described above. In this experiment, the purity of acetylene, oxygen and methane was 99.9995%, and the purity of hydrogen, nitrogen, and carbon dioxide was 99.9999%. The obtained results are shown in the adsorption isotherms illustrated in FIGS. 3A, 3B, 4A, and 4B.

Referring to FIGS. 3A, 3B, 4A, and 4B, at 760 torr at 0☐ or room temperature, the amounts of the hydrogen, nitrogen, methane, and oxygen adsorbed onto the microporous metal formates were small, but the amount of the acetylene adsorbed onto the microporous metal formates was large. Therefore, it can be identified that acetylene can be selectively adsorbed and separated from a gaseous mixture.

(2) Separation of Acetylene Using Microporous Mn-Formate

Figure 5:
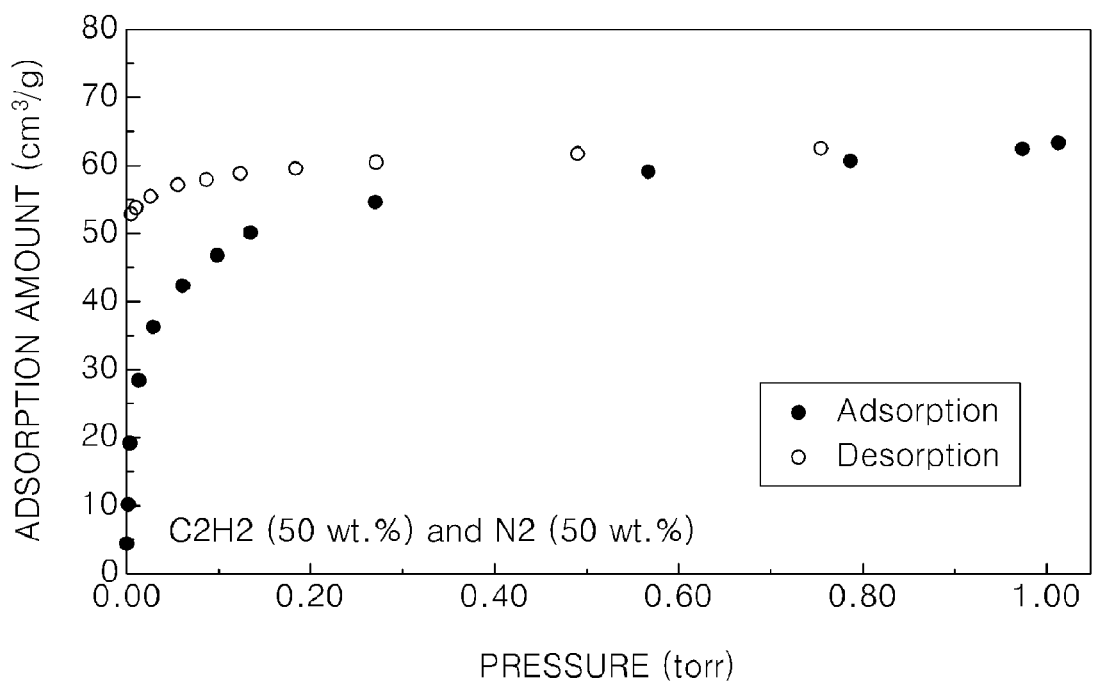
FIG. 5 is a graph showing adsorption isotherms using microporous Mn formate prepared according to Example 2 for a gaseous mixture of acetylene and nitrogen in which "○" denotes results of detachment.

A gaseous mixture including nitrogen and acetylene in a volume ratio of 50:50 was adsorbed onto a microporous Mn-formate in the same manner as in Example 1 at 196K while the pressure was slowly increased from $10^{-5}$ bar to 1 bar. When the temperature was not changed by 0.0008 atm or more for the equilibrium time of 5 minutes, the pressure was measured to calculate the volume of gaseous mixture adsorbed onto the microporous metal formate with respect to each adsorption or desorption data point. The obtained results are shown in the adsorption isotherm illustrated in FIG. 5.

The adsorbed gas was analyzed using a carbon analyzer (Baseline-MOCON, Model: 8800TCA, minimum detection amount: 0.1 ppm or more). As a result, no nitrogen was detected and only acetylene was detected.

Example 3

Storage and Separation of Oxygen Using Microporous Mn-Formate (1) Adsorption Isotherms of Microporous Mn-Formate in which Oxygen and Nitrogen were Adsorbed Nitrogen and oxygen were adsorbed onto the same manner as in Example 1 at 77K using 250 g of microporous Mn-formate. To prevent condensation of oxygen at 77K, saturated vapors of oxygen and nitrogen were maintained at pressures of 156 torr or less and 760 torr or less, respectively. When the pressure was not changed by 0.008 atm or more for the equilibrium time of 5 minutes, the pressure was measured to calculate the volume of gaseous mixture adsorbed onto the microporous metal formate with respect to each adsorption or desorption data point. The obtained adsorption isotherm results are shown in FIG. 6.

Referring to FIG. 6, at low temperature, the microporous Mn formate adsorbs a much greater amount of oxygen compared to nitrogen. Therefore, it can be seen that oxygen can be selectively separated from a mixture of nitrogen and oxygen.

(2) Separation of Oxygen Using Microporous Mn-Formate

Figure 7:
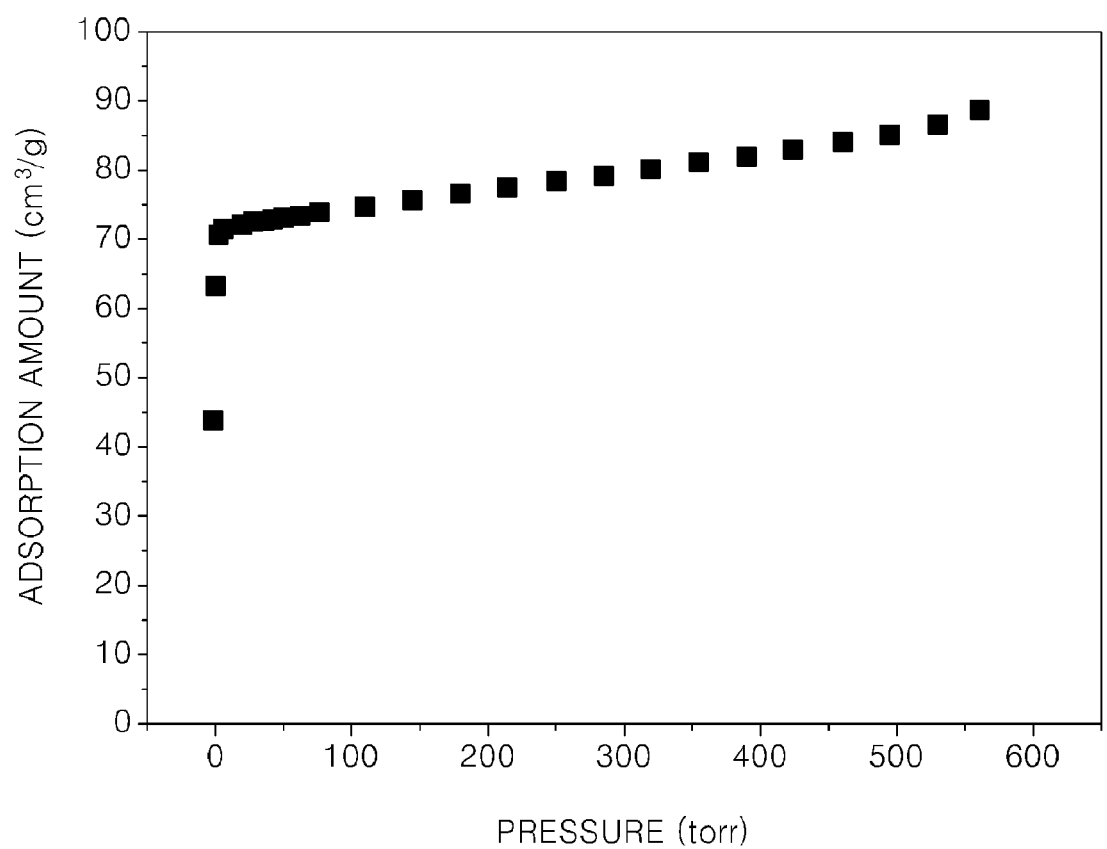
FIG. 7 is a graph showing adsorption isotherms of a microporous Mn-formate prepared according to Example 3 with respect to a gaseous mixture of acetylene and nitrogen.

A gaseous mixture of oxygen and nitrogen in a volume ratio of 50:50 was adsorbed onto a microporous Mn-formate at 87K. The obtained adsorption isotherm is shown in FIG. 7.

The adsorbed gas was analyzed using an oxygen analyzer (Model: Oxy-100, degree of precision: ±0.5%). As a result, the purity of the adsorbed oxygen was 99.5%.

According to a method of storage of acetylene according to the disclosed embodiments, a large amount of acetylene can be stably stored at room temperature or lower. In addition, the method of storing acetylene does not use a solvent such as acetone or DMF as a storage medium, and thus, inclusion of the solvent as an impurity in the recollecting process of acetylene can be prevented.

According to the method of separating acetylene of the disclosed embodiments, a microporous metal formate selectively adsorbs acetylene included in a gaseous mixture. Therefore, acetylene that is necessarily used to synthesize 1,4-butanediol which is necessarily used to obtain polyurethane and polyester plastics can be obtained in a high degree of purity.

Also, according to methods of separating and storing oxygen according to the disclosed embodiments, microporous metal formates adsorb a much greater amount of oxygen compared to nitrogen, and thus, oxygen can be selectively separated from a mixture of nitrogen and oxygen and stored.

While the disclosed embodiments have been particularly shown and described with reference to exemplary embodiments thereof, it will be understood by those of ordinary skill in the art that various changes in form and details may be made therein without departing from the spirit and scope of the disclosed embodiments as defined by the following claims.

What is claimed is:

1. A method of storing acetylene, comprising contacting acetylene or an acetylene-containing gaseous mixture with microporous metal formates represented by Formula 1 so as to adsorb acetylene onto the microporous metal formates: where each formate ion is bound to three metallic ions Ms, each metallic ion M is bound to six formate ions, a composition ratio of the metallic ion M to the formate ion is 1:2, and the metal is Mg, Mn, Co, Zn, Ni or Fe.

2. A method of separating acetylene, comprising contacting an acetylene-containing gaseous mixture with microporous metal formates represented by Formula 1 so as to selectively adsorb acetylene onto the microporous metal formates: where each formate ion is bound to three metallic ions Ms, each metallic ion M is bound to six formate ions, a composition ratio of the metallic ion M to the formate ion is 1:2, and the metal is Mg, Mn, Co, Zn, Ni or Fe.

3. The method of claim 2, wherein the gaseous mixture further comprises at least one gas selected from the group consisting of hydrogen, nitrogen, oxygen, methane, carbon dioxide, monoxide, $SF_6$, NO, $N_2O$, $NO_2$, $H_2S$, $SO_2$, $Cl_2$, krypton, neon, zenon, and helium.

4. The method of claim 2, wherein the gaseous mixture is contacted with the microporous metal formates at a temperature of 196K to 325K.

* * * * *

UNITED STATES PATENT AND TRADEMARK OFFICE
CERTIFICATE OF CORRECTION

PATENT NO. : 7,771,513 B2
APPLICATION NO. : 12/026004
DATED : August 10, 2010
INVENTOR(S) : Kim et al.

It is certified that error appears in the above-identified patent and that said Letters Patent is hereby corrected as shown below:

Title Page, Column 1 (Inventors), Line 5, delete "(FR)" and insert -- (KR) --, therefor.

Column 8, line 39 (Approx.), Claim 1, after "formates" insert
<Formula 1>

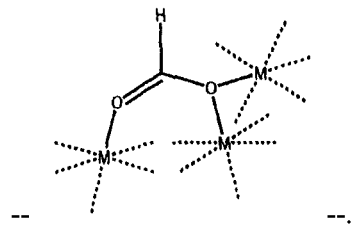

Column 8, line 48 (Approx.), Claim 2, after "formates" insert
<Formula 1>

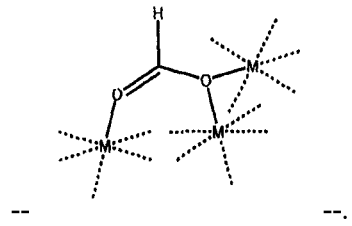

Column 8, lines 55-56, Claim 3, delete "SF.sub.6, NO, N.sub.2O, NO.sub.2, H.sub.2S, SO.sub.2, Cl.sub.2," and insert -- $SF_6$, NO, $N_2O$, $NO_2$, $H_2S$, $SO_2$, $Cl_2$, --, therefor.

Signed and Sealed this
First Day of March, 2011

David J. Kappos
*Director of the United States Patent and Trademark Office*